US008730469B2

(12) United States Patent
Umapathy et al.

(10) Patent No.: US 8,730,469 B2
(45) Date of Patent: May 20, 2014

(54) METHOD FOR DETECTING VIBRATIONAL STRUCTURE OF A MOLECULE AND A SYSTEM THEREOF

(75) Inventors: Siva Umapathy, Bangalore (IN); Yapamanu Adithya Lakshmanna, Bangalore (IN); Babita Mallick, Bangalore (IN)

(73) Assignee: Indian Institute of Science, Bangalore (IN)

( * ) Notice: Subject to any disclaimer, the term of this patent is extended or adjusted under 35 U.S.C. 154(b) by 568 days.

(21) Appl. No.: 13/054,677

(22) PCT Filed: Jul. 17, 2009

(86) PCT No.: PCT/IN2009/000405
§ 371 (c)(1),
(2), (4) Date: Jan. 18, 2011

(87) PCT Pub. No.: WO2010/007630
PCT Pub. Date: Jan. 21, 2010

(65) Prior Publication Data
US 2011/0134422 A1 Jun. 9, 2011

(30) Foreign Application Priority Data

Jul. 17, 2008 (IN) .......................... 01723/CHE/2008

(51) Int. Cl.
*G01J 3/44* (2006.01)
(52) U.S. Cl.
USPC ........................................................ 356/301
(58) Field of Classification Search
USPC ..................... 356/300–334, 72, 73
See application file for complete search history.

(56) References Cited

U.S. PATENT DOCUMENTS

| 7,398,119 B2 * | 7/2008 | Lambert et al. ............... 600/473 |
| 7,705,989 B2 * | 4/2010 | Chaton et al. ................. 356/445 |
| 2005/0280827 A1 * | 12/2005 | Potma et al. .................. 356/485 |
| 2010/0027000 A1 * | 2/2010 | Pestov et al. .................. 356/301 |
| 2010/0046039 A1 * | 2/2010 | Xie et al. ....................... 358/471 |

OTHER PUBLICATIONS

Ploetz, et al. "Femtosecond stimulated Raman microscopy" Applied Physics B 87, 389-393 (2007).*
McCamant et al. "Femtosecond Time-Resolved Stimulated Raman Spectroscopy: Application to the Ultrafast Internal Conversion in β-Carotene" Journal of Physical Chemistry A., Oct. 9, 2003; 104(40):8208-8214.*
Cheng et al.; "Coherent Anti-Stokes Raman Scattering Microscopy: Instrumentation, Theory, and Applications;"*J. Phys. Chem. B*; 2004; vol. 108; pp. 827-840.
Begley et al., "Coherent anti-Stokes Raman spectroscopy," *Applied Physics Letters*; 1974; vol. 25, No. 7; pp. 387-390.
Matousek et al.; "Efficient Rejection of Fluorescence from Raman Spectra Using Picosecond Kerr Gating;"*Applied Spectroscopy*; 1999, vol. 53, No. 12; pp. 1485-1489.

(Continued)

*Primary Examiner* — Gregory J Toatley
*Assistant Examiner* — Dominic J Bologna
(74) *Attorney, Agent, or Firm* — Oliff PLC

(57) ABSTRACT

The present invention relates to a method for detecting vibrational structure of a molecule by generation of the Loss signals with the help of interaction of White Light Continuum (WL) and narrow spectral width picosecond pulse on the surface of the sample, known as Ultrafast Raman Loss Spectroscopy (URLS). The invention further defines a system for generation of Loss signals for detection of the vibrational structure of a molecule.

22 Claims, 19 Drawing Sheets

(56) References Cited

OTHER PUBLICATIONS

Figure 1:
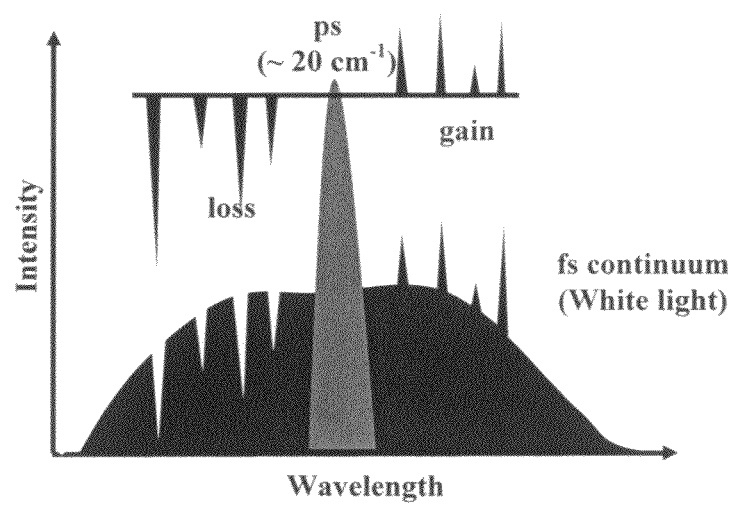

Arzhantsev et al.; "Design and Characterization of a Femtosecond Fluoescence Spectrometer Based on Optical Kerr Gating;" *Applied Spectroscopy*; 2005; vol. 59, No. 2; pp. 206-220.

Owyoung; "Coherent Raman Gain Spectroscopy Using CW Laser Sources;"*IEEE Journal of Quantum Electronic*; 1978;vol. QE-14, No. 3; pp. 192-203.

Wong et al.; "Stimulated Raman Gain Spectroscopy Seeded by Amplified Spontaneous Emission;"*Journal of Raman Spectroscopy*; 1992; vol. 23; pp. 479-481.

Yoshizawa et al.; "Femtosecond time-resolved resonance Raman gain spectroscopy in polydiacetylene;" *Physical Review B*; 1994; vol. 49, No. 18; pp. 259-262.

Yoshizawa et al.; "Femtosecond time-resolved Raman spectroscopy using stimulated Raman scattering;"*Physical Review A*; 1999; vol. 61; pp. 013808-1-013808-6.

Rondonuwu et al.; "Internal-conversion and radiative-transition processes among the $1B_u^+$; $1B_u^-$ and $2A_g^-$ states of all-*trans*-neurosporene as revealed by subpicosecond time-resolved Raman spectroscopy;" *Chemical Physics Letters*; 2002; vol. 357; pp. 376-384.

McCamant et al.; "Femtosecond Broadband Stimulated Raman: A New Approach for High-Performance Vibrational Spectroscopy;" *Applied Spectroscopy*; 2003; vol. 57, No. 11; pp. 1317-1323.

Jin et al.; "Development of Femtosecond Stimulated Raman Spectroscopy: Stimulated Raman Gain via Elimination of Cross Phase Modulation;" *Bull. Korean Chem. Society*; 2004; vol. 25, No. 12; pp. 1829-1832.

Laimgruber et al.; "A femtosecond stimulated raman spectrograph for the near ultraviolet;"*Applied Physics B—Lasers and Optics*; 2006; vol. 85; pp. 557-564.

Mallick et al.; "Design and development of stimulated Raman spectroscopy apparatus using a femtosecond laser system;" *Current Science*; 2008; vol. 95, No. 11; pp. 1551-1559.

Druet et al.; "Cars Spectroscopy;" *Progress in Quantum Electronics*; 1981; vol. 7; pp. 1-72.

Fleming et al.; "A Practical Analysis for Coherent Anti-Stokes Raman Scattering (CARS) Spectra;" *Journal of Raman Spectroscopy*; 1979; vol. 8, No. 5; pp. 284-290.

Tolles et al.; "A Review of the Theory and Application of Coherent Anti-Stokes Raman Spectroscopy (CARS);" *Applied Spectroscopy*; 1977; vol. 31, No. 4; pp. 253-271.

Umapathy et al; "Ultrafast Raman loss spectroscopy;"*J. Raman Spectroscopy*; 2009; vol. 40; pp. 235-237.

Umapathy et al; "Femtosecond dynamics from Raman spectroscopy: a contemporary view;"*Plenary Lectures, Proceedings of ICORS 2008*; London; pp. 14-19.

Umapathy et al; "Mode-dependent dispersion in Raman line shapes: Observation and implications from ultrafast Raman loss spectroscopy;" *The Journal of Chemical Physics*; 2010; vol. 133; pp. 024505-1-024505-6.

Seifert et al.; "Observation of low-frequency Raman and Kerr effect contributions in picosecond infrared pump probe experiments;" *Vibrational Spectroscopy*; 2000; vol. 23; pp. 219-230.

An et al.; "In situ determination of fluorescence lifetimes via inverse Raman scattering;" *Optics Communications*; 2002; vol. 202; pp. 209-216.

Frontiera et al.; "Origin of negative and dispersive features in anti-Stokes and resonance femtosecond stimulated Raman spectroscopy;" *The Journal of Chemical Physics*; 2008; vol. 129; pp. 064507-1-064507-6.

Angeloni et al.; Resonance Raman Spectrum of Crystal Violet; Journal of Raman Spectroscopy; 1979; vol. 8, No. 6; pp. 305-310.

McCamant et al.; "Femtosecond Time-Resolved Stimulated Raman Spectroscopy: Application to the Ultrafast Internal Conversion in β-Carotene;" *J. Phys. Chem A.*; 2003; vol. 107, No. 40; pp. 8208-8214.

International Search Report issued in PCT/IN2009/000405 dated Nov. 6, 2009.

* cited by examiner

METHOD FOR DETECTING VIBRATIONAL STRUCTURE OF A MOLECULE AND A SYSTEM THEREOF

FIELD OF THE INVENTION

The present invention relates to a method for detecting vibrational structure of a molecule by generation of the Loss signals with the help of interaction of White Light Continuum (WL) and narrow spectral width picosecond pulse on the surface of the sample, known as Ultrafast Raman Loss Spectroscopy (URLS). The invention further defines a system for generation of Loss signals for detection of the vibrational structure of a molecule.

BACKGROUND AND PRIOR ART OF THE INVENTION

Light on interaction with matter undergoes scattering. Most of the incident photons are elastically scattered (Rayleigh scattering) while one out of ten million are inelastically scattered. Inelastic scattering of photon is termed as Raman scattering. Raman scattering occurs due the change in the polaraizability of a molecule thereby leading to a change in its vibrational state. This results in the emission of a photon having energy lower (Stokes Raman) or higher (anti-Stokes Raman) than that of the incident photon depending upon the initial vibrational state of the molecule. The shift in Raman frequency provides chemical and structural information. However, Raman scattering is relatively weak leading to low detection sensitivity and in consequence, it's difficult to measure low concentrations and weak Raman scatterer. This can be overcome using Resonance Raman (RR) technique wherein the wavelength of the exciting photon lies within the electronic absorption of the molecular system. Under this condition, the Raman signals can be enhanced by a factor of $10^2$ to $10^4$. But, in case of fluorescent molecules or presence of fluorescent impurities, the strong fluorescence signal masks the weak Raman signals.

However, owing to its low scattering cross-section one needs to accumulate for longer time to obtain good signal. Thus, the routine application of spontaneous Raman spectroscopy for the vibrational structure determination is limited to non-fluorescent materials with relatively strong Raman cross-section.

Advanced Raman spectroscopic techniques, such as coherent anti-Stokes Raman scattering (CARS)[1], picosecond (ps) Kerr-gate[2], stimulated Raman scattering (SRS)[3-11], etc. have been developed to overcome these problem. All these processes are characterized by the third order nonlinear susceptibility ($\chi^{[3]}$) of the system. Both CARS and SRS involve a four wave mixing process providing the signal. While in ps Kerr gate spectroscopy, a nonlinear phenomenon, Kerr effect, is used as a gate for the detection of the instantaneous Raman scattering signals before being overwhelmed by the fluorescence signal. Kerr effect occurs due to a nonlinear change in the refractive index of a material in the presence of a short laser pulse (gating pulse). These methods provide Raman spectrum with a good signal to noise ratio and efficient fluorescence rejection compared to conventional Raman spectroscopy. Yet, these methods suffer from some difficulties.

For example, in Kerr-gate technique[2], fluorescence cannot be completely eliminated and background signal from long-lived samples add to the noise. While CARS efficiency is much greater than that of spontaneous Raman scattering, its sensitivity is limited by structureless background arising from a non-resonant component of the third order susceptibility. In dilute solutions, this background signal is due to solvent molecules. This non-resonant background leads to a distorted dispersed signal. In addition, a CARS signal is directly proportional to the square of the spontaneous Raman spectrum. This has effect of enhancing the strong features at the expense of the weaker ones. Further, CARS experiment requires the interacting laser beams to follow a specific phase matching condition, rendering the technique extremely sensitive to alignment of laser beams and the angles of interaction.

All of the patents related to analytical applications of Raman spectroscopy or its derivations, used for structure elucidation, discuss only the positive signal (GAIN) in Raman Spectroscopy. The instant invention is very unique in observation of the signals as LOSS with more intensity than the GAIN (positive signal).

There are patents related to LOSS observation and utility in optical communications by fibers, which are related to modulation of ACOUSTIC FREQUENCY signals, unlike what the present invention where modulation of LIGHT FREQUENCY leads to vibrational structural information of system under study. This is a significant difference, since the technology for generation and detection of both, acoustic and light signals are entirely different.

SUMMARY OF THE INVENTION

Accordingly, the present invention relates to a method for detecting vibrational structure of a molecule, said method comprising steps of (a) generating White Light Continuum (WL) probe and picosecond pump, and (b) focusing the WL probe and picosecond pump onto a sample to detect the vibrational structure of the molecule; and a system for detection of vibrational structure of a molecule, said system comprising of (a) a femtosecond source having a light source input, wherein the femtosecond source is configured to generate a femtosecond pulse, (b) a spectral filter receives the femtosecond pulse generated by the femtosecond source to produce a picosecond pulse, and a crystal unit along with a short wave pass filter receives the femtosecond pulse generated by the femtosecond source to produce white light continuum, (c) a sample unit receives the picosecond pulse and the white light continuum to provide a signal output, and (d) a spectrometer takes the signal output generated from the sample unit to produce a signal in spectral domain and a detector to detect vibrational structure of molecule by creating image of the spectral domain signal.

BRIEF DESCRIPTION OF THE ACCOMPANYING FIGURES

FIG. 1: Ultra-fast Raman loss and stimulated Raman scattering.

Figure 2A:
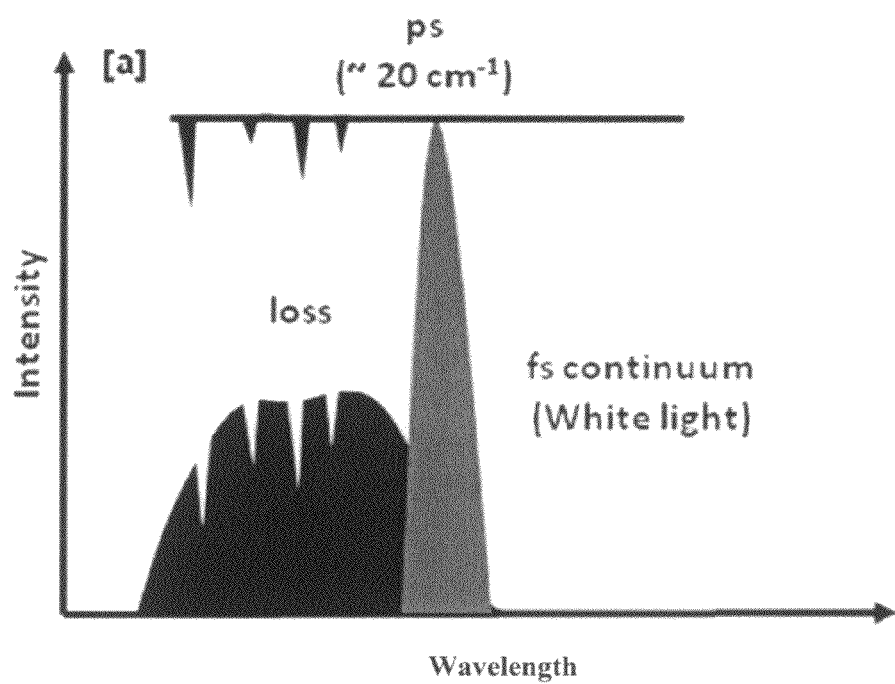

FIG. 2a: Blocking of the red region using a short wave pass filter.

Figure 2B:
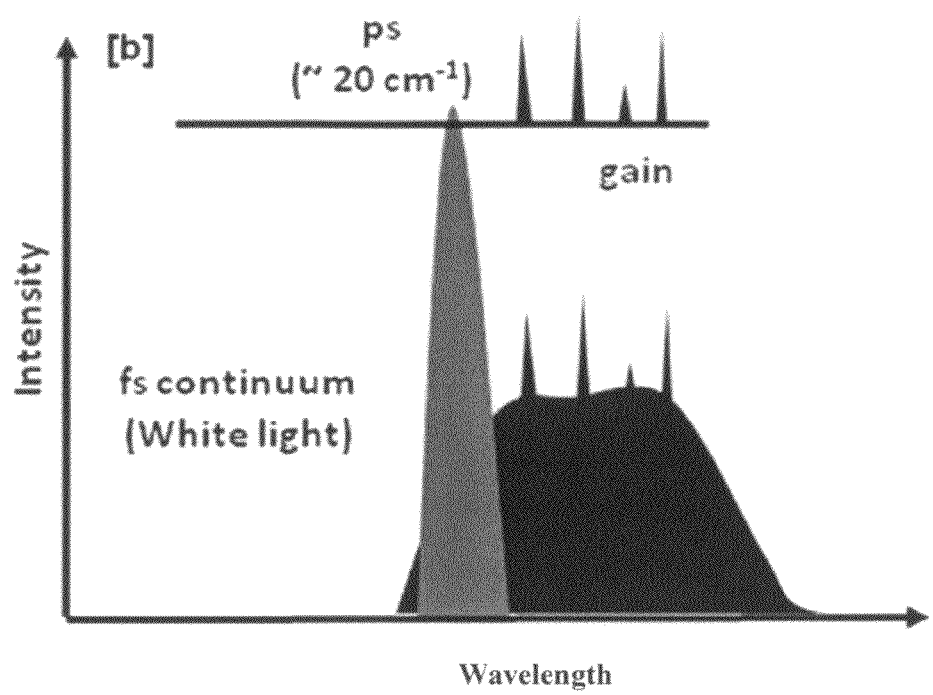

FIG. 2b: Blocking of the blue region using a long wave pass filter.

Figure 3:
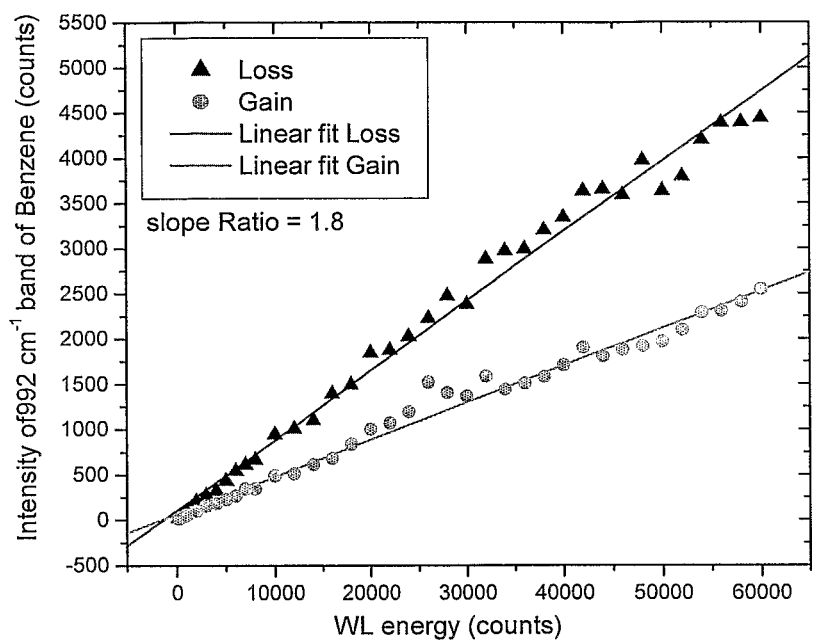

FIG. 3: URLS and SRS signal intensity change for 992 $cm^{-1}$ band of benzene with the variation in power of WL.

Figure 4:
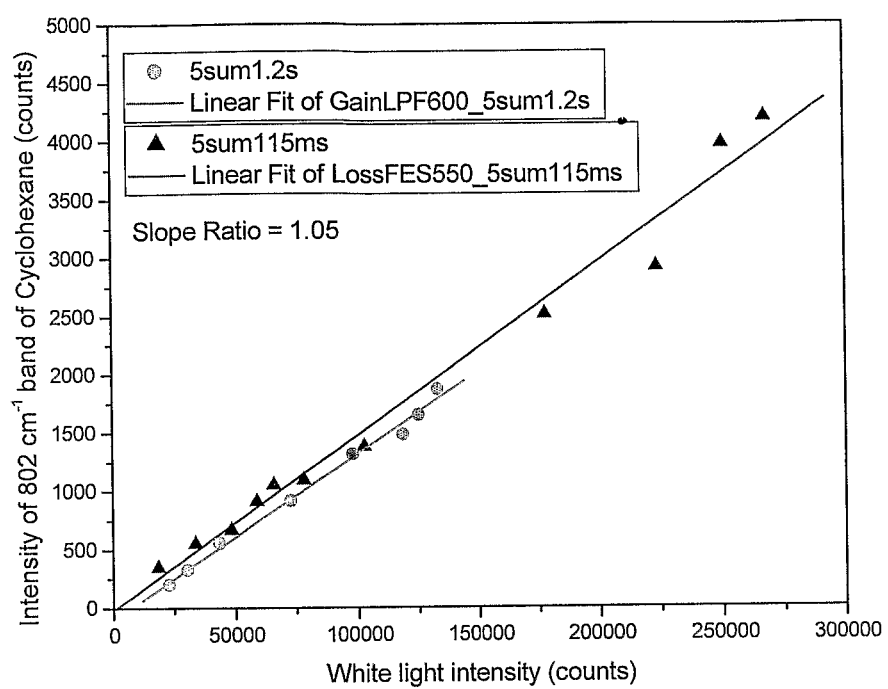
Figure 5:
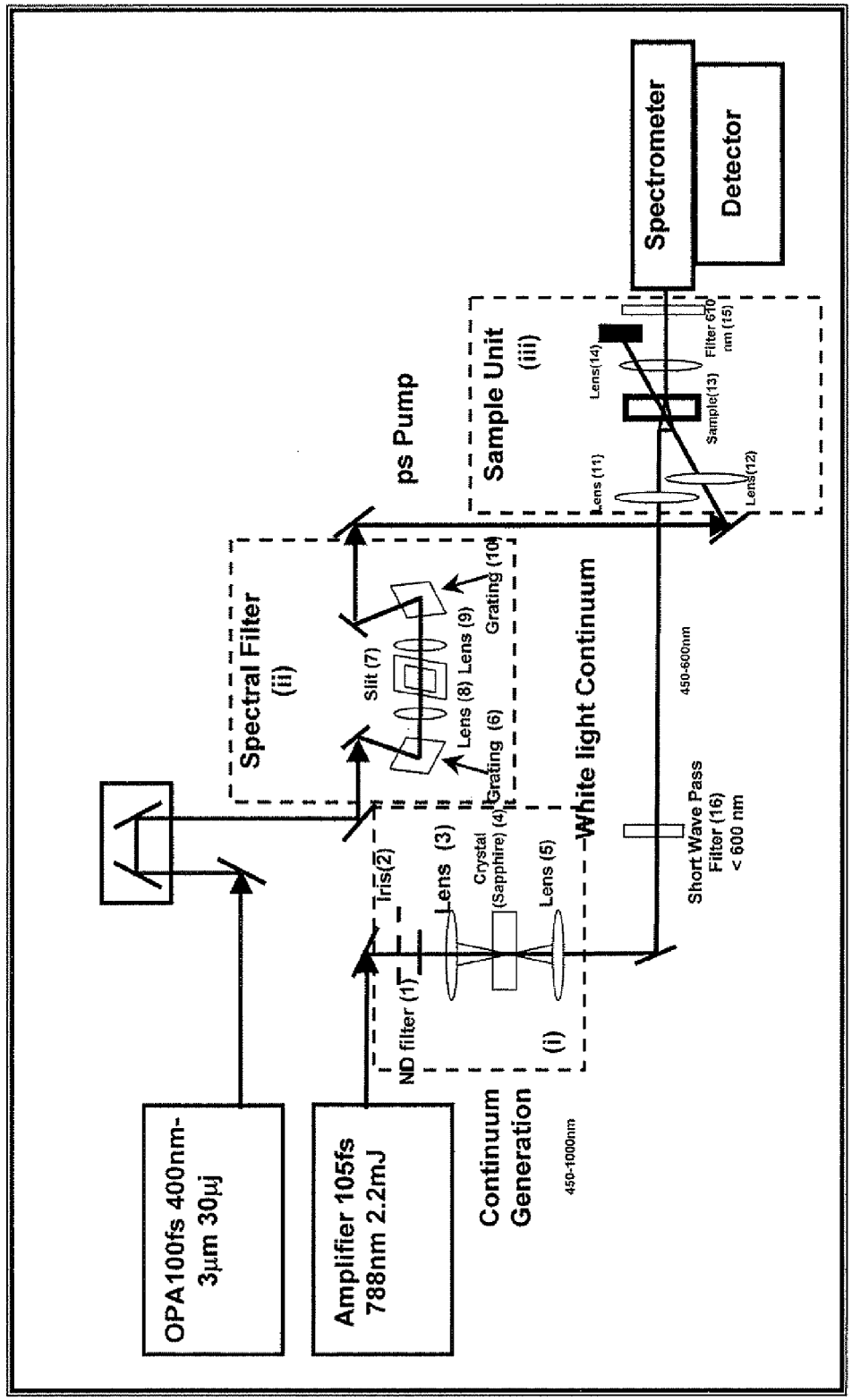

FIG. 4: Change observed in the URLS and SRS signal intensities for 802 $cm^{-1}$ band of cyclohexane with variation in WL power with filters to allow WL specific to region of observation FIG. 5: Experimental set-up for performing Ultrafast Raman. Loss Spectroscopy.

Figure 6:
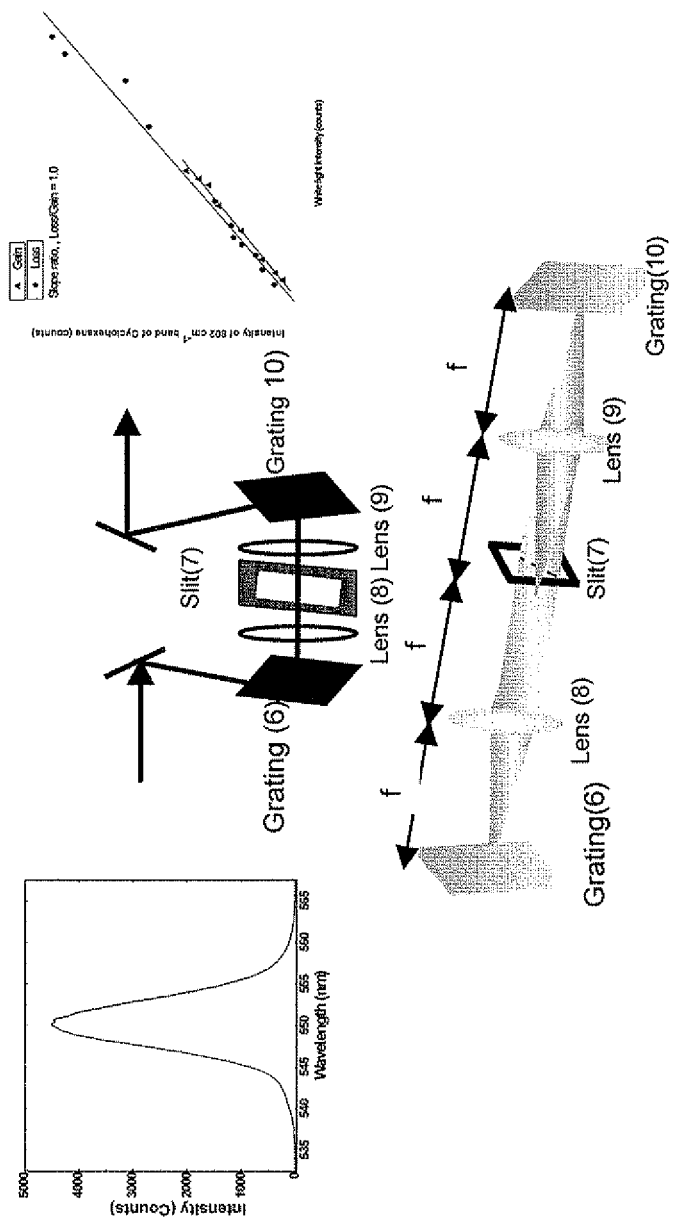

FIG. 6: Experimental set-up of the spectral filter used in the invention.

Figure 6A:
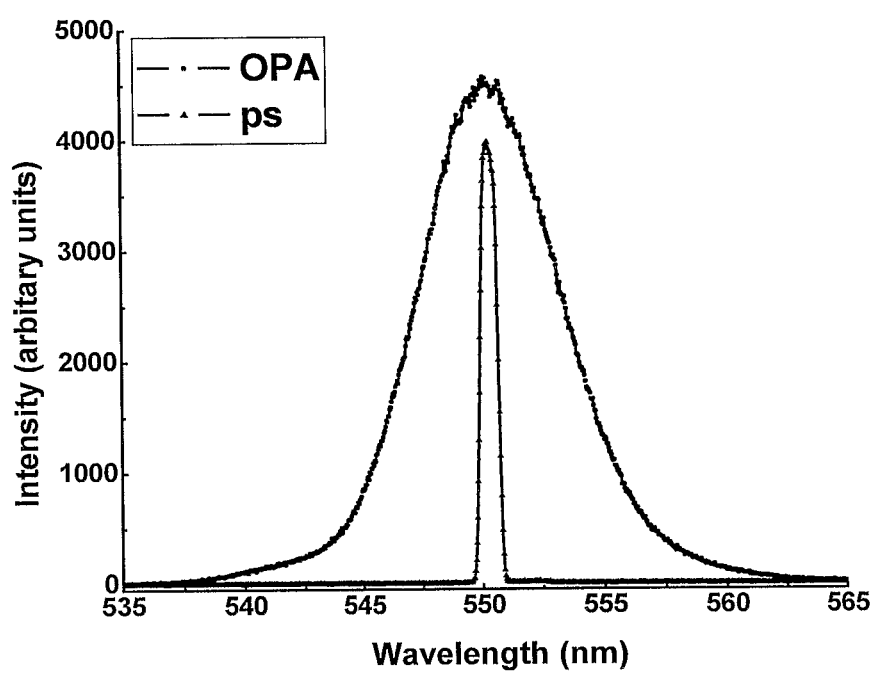

FIG. 6a: OPA (dash-circle-dash) and ps pulses (dash-triangle-dash) spectra.

Figure 7:
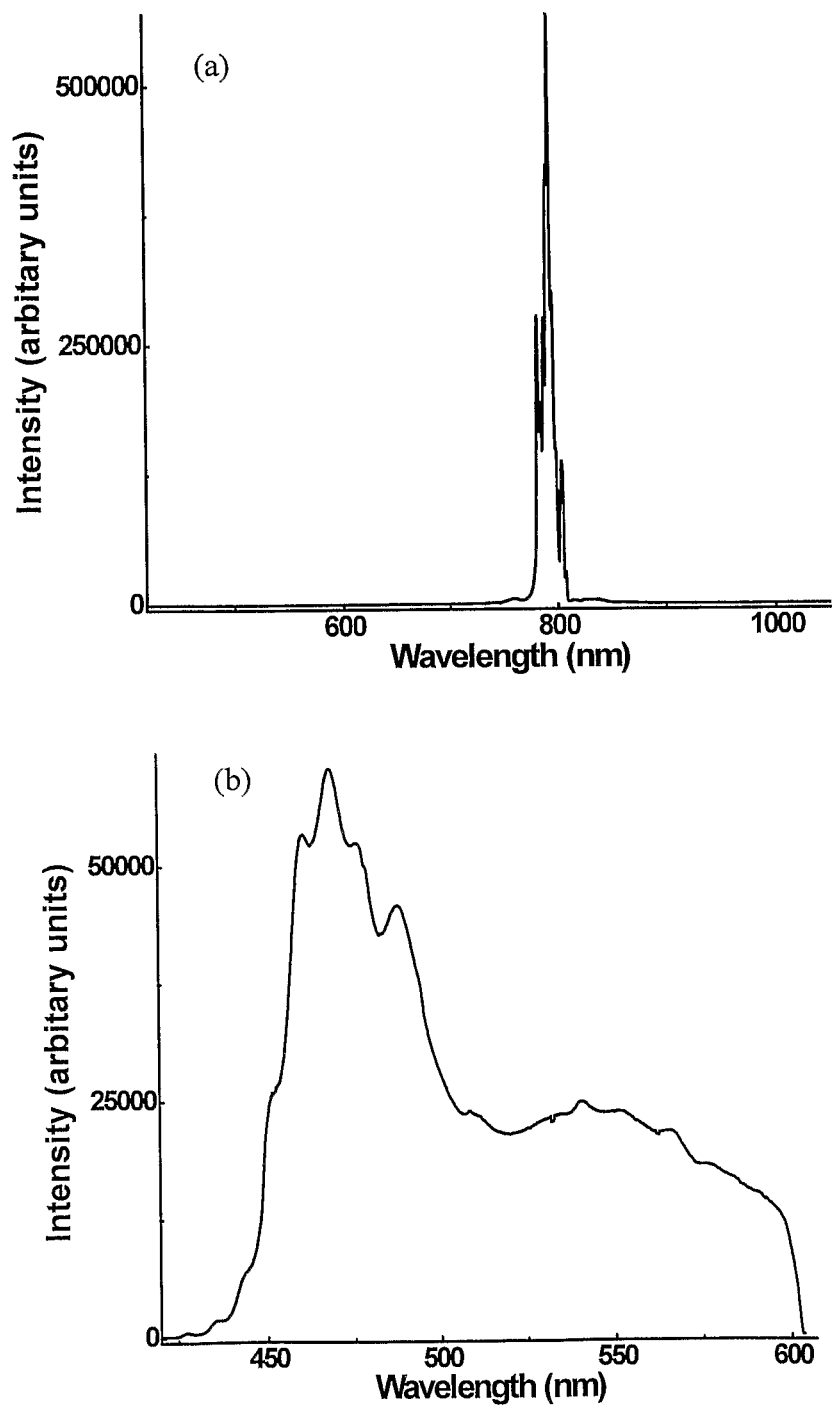

FIG. 7: White light (a) without filter and (b) with short wave pass filter FES0600

Figure 8:
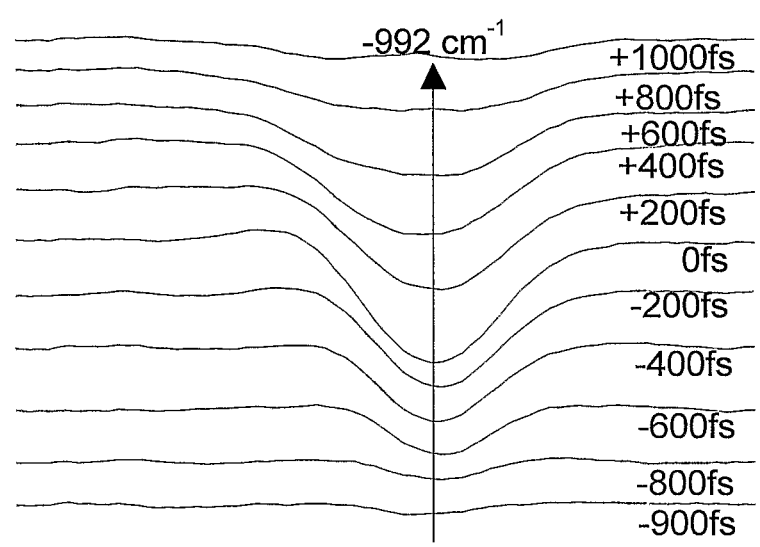

FIG. 8: Change in URLS signal of the −992 cm$^{-1}$ peak of benzene with the change in delay between the ps pulse and WL FIG. 9a: URLS spectra of various systems; (a) Chloroform (CHCl$_3$), (b) Dimethyl Sulphoxide (DMSO), (c) Acetonitrile (ACN), (d) Cyclohexane (CH) and (e) Crystal violet (CV) solution in ethanol. (solvent peaks are marked as *)

Figure 9A:
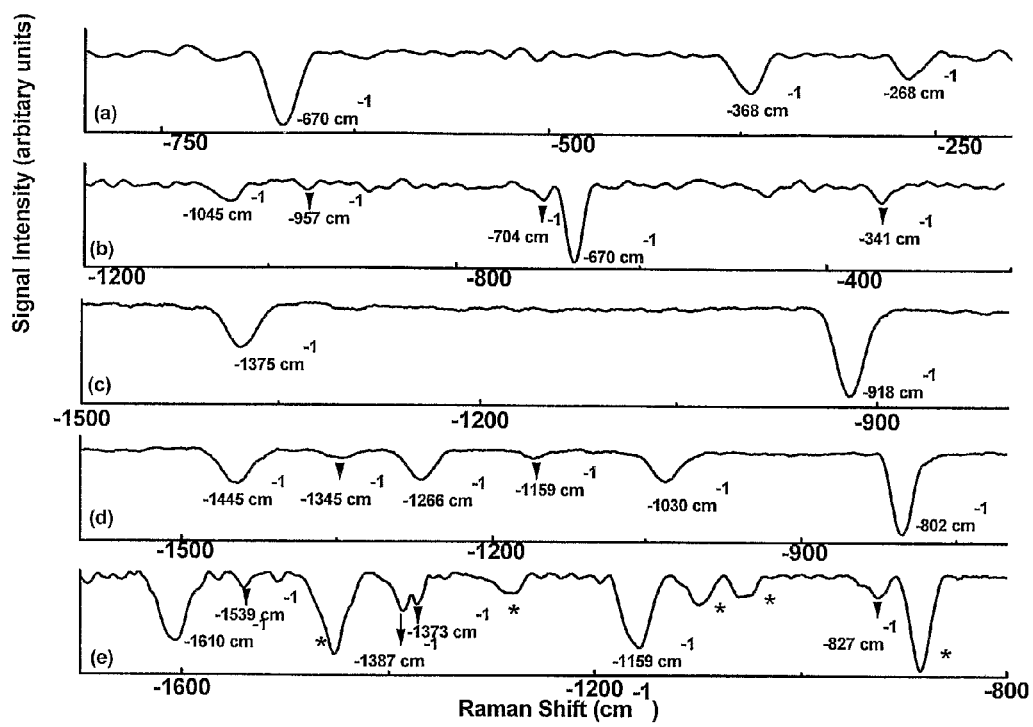
Figure 9B:
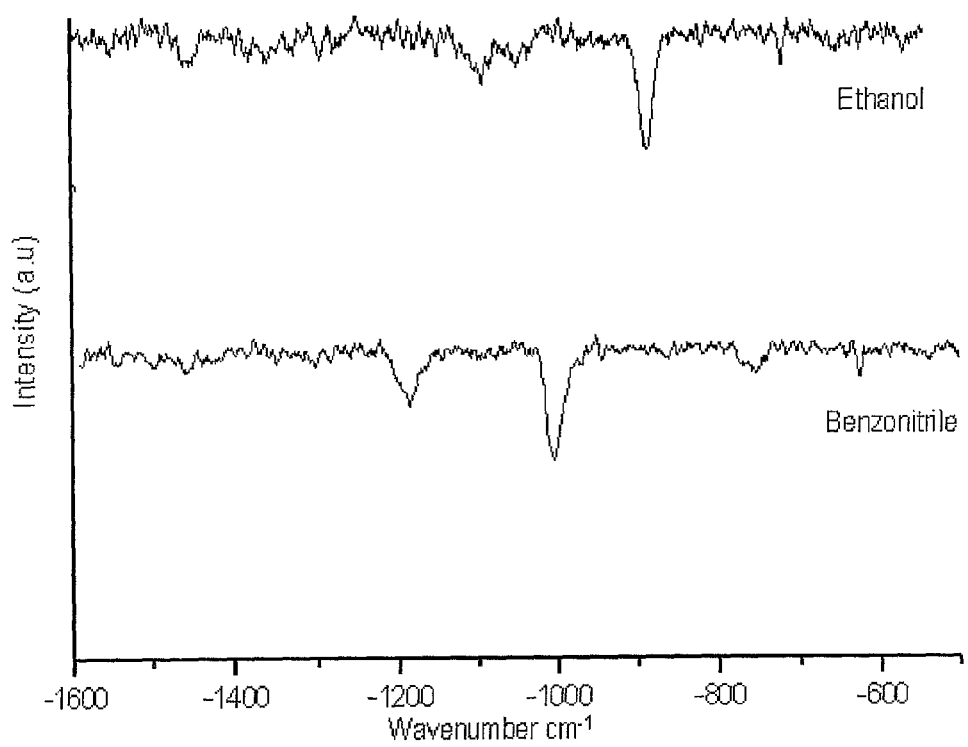

FIG. 9b: URLS spectra of Benzonitrile and Ethanol.

Figure 9C:
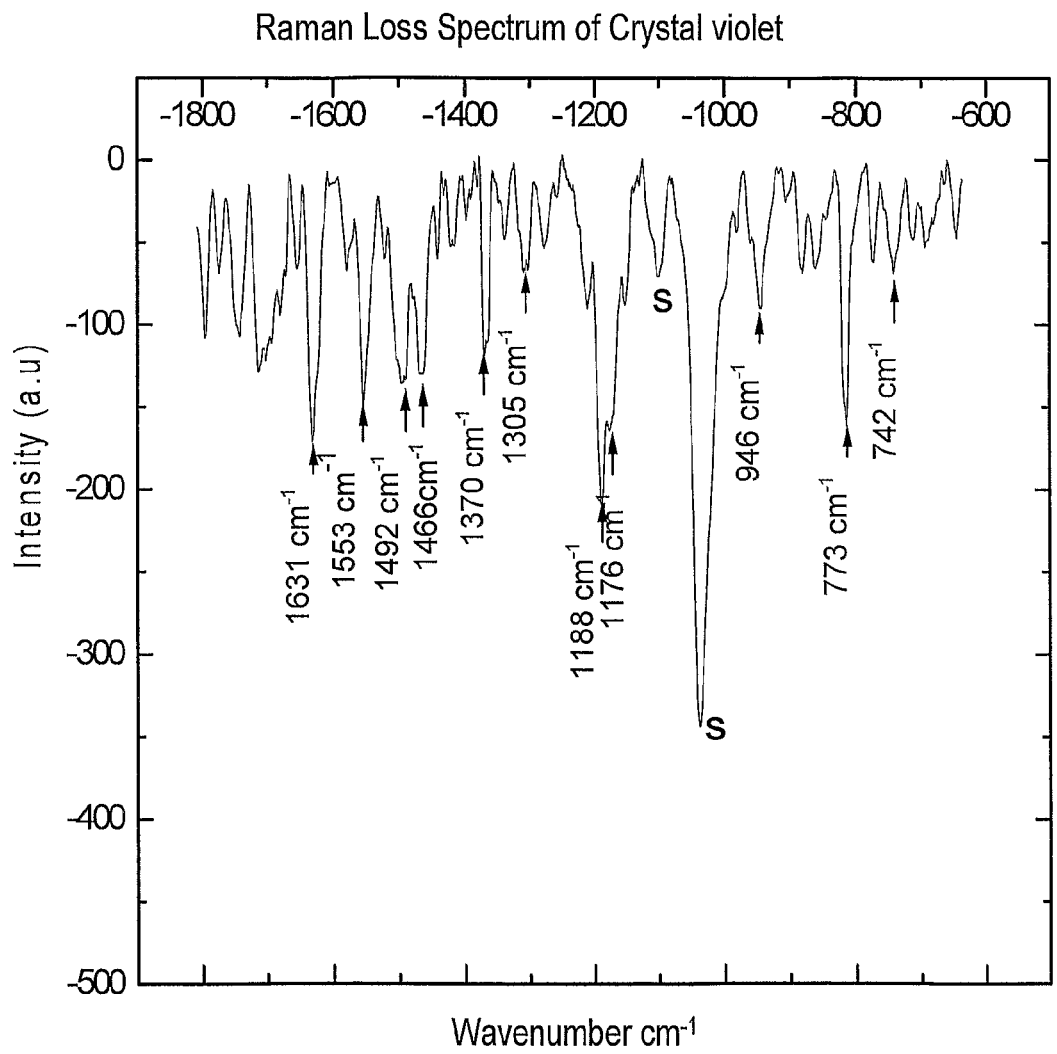

FIG. 9c: URLS spectra of Crystal Violet in ethanol. (solvent peaks are marked as 's')

Figure 10:
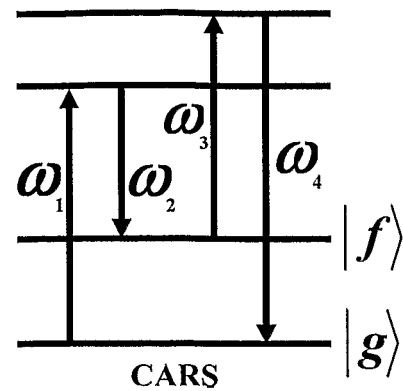
Figure 10:
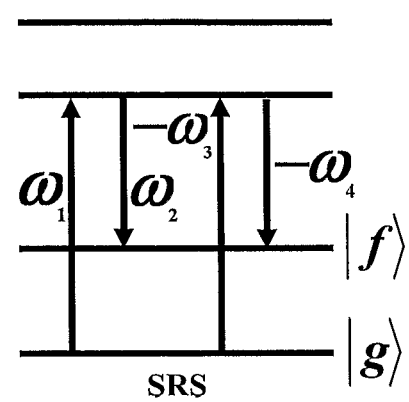

FIG. 10: Energy level diagram involved in CARS and SRS.

Figure 11:
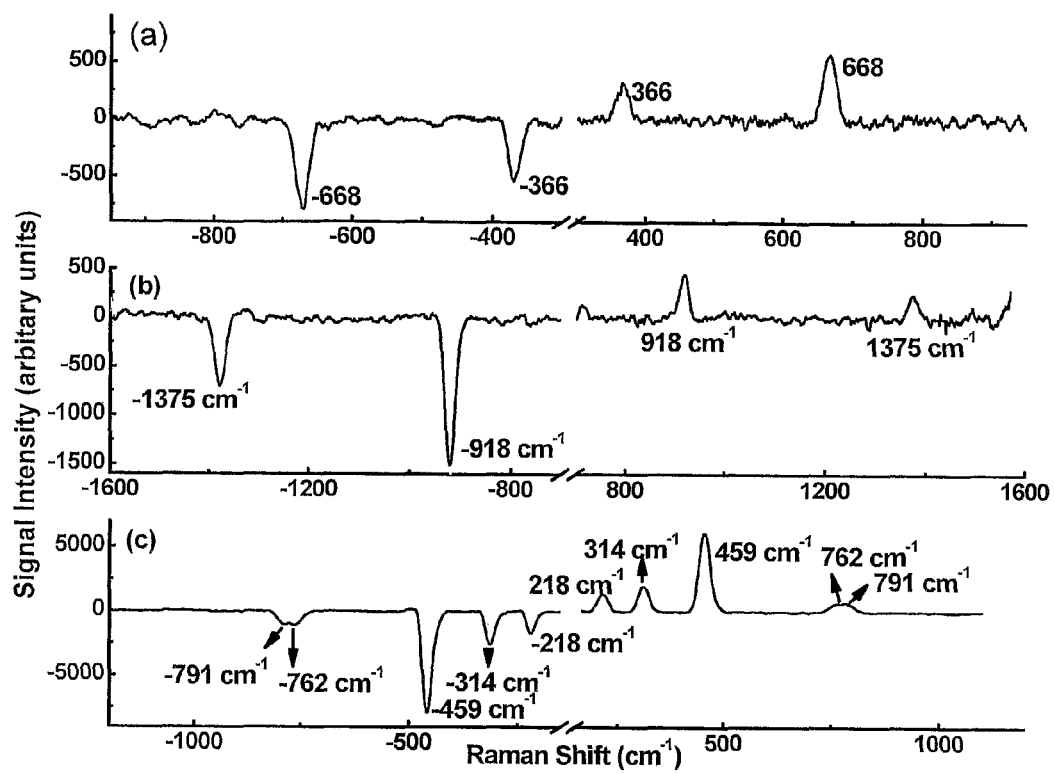

FIG. 11: Comparison of URLS and SRS spectra of (a) CHCl$_3$, (b) ACN and (c) CCl4.

Figure 12:
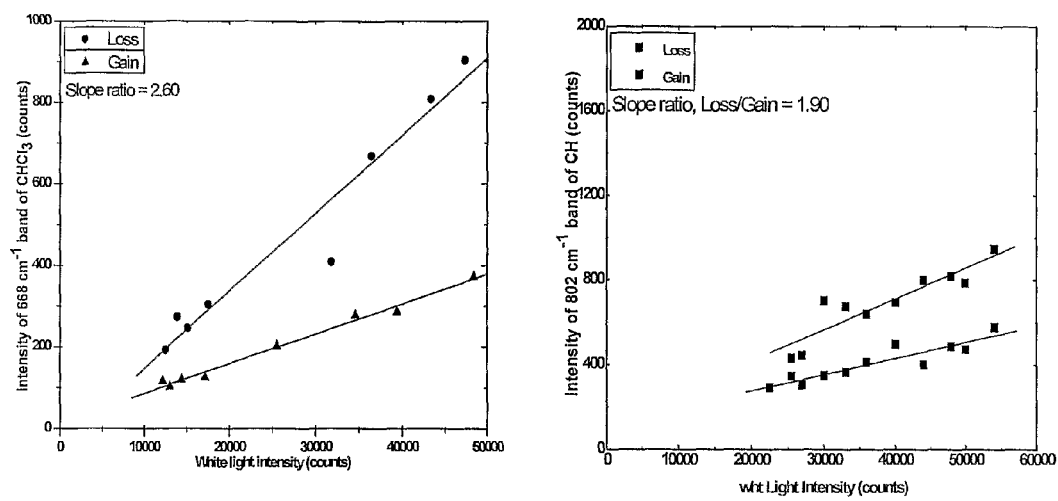

FIG. 12: URLS and SRS signal intensity v/s WL power. [R.H.S. for Chloroform (CHCl$_3$) and L.H.S. for Cyclohexane (CH)].

Figure 13:
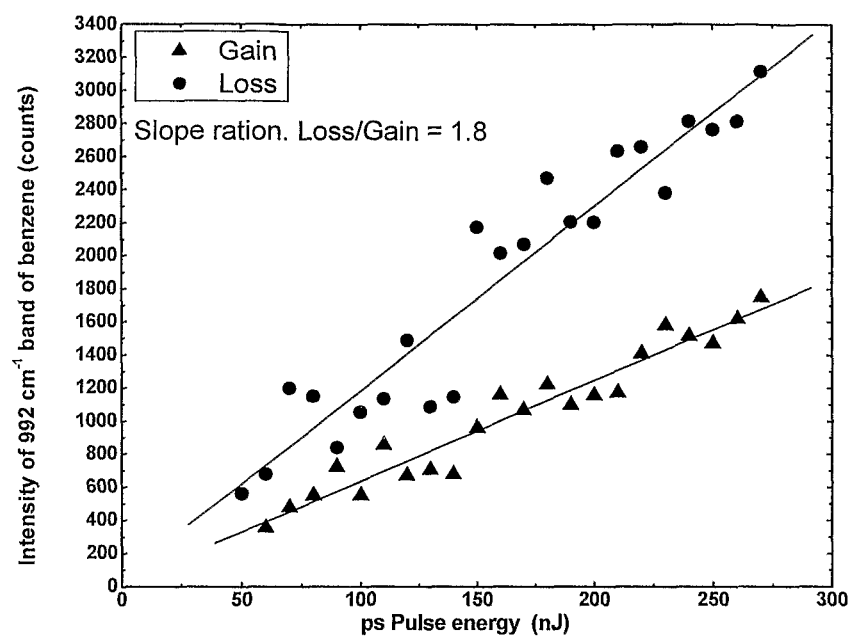

FIG. 13: URLS and SRS signal intensity of the 992 cm$^{-1}$ peak of benzene v/s ps pulse power.

Figure 14:
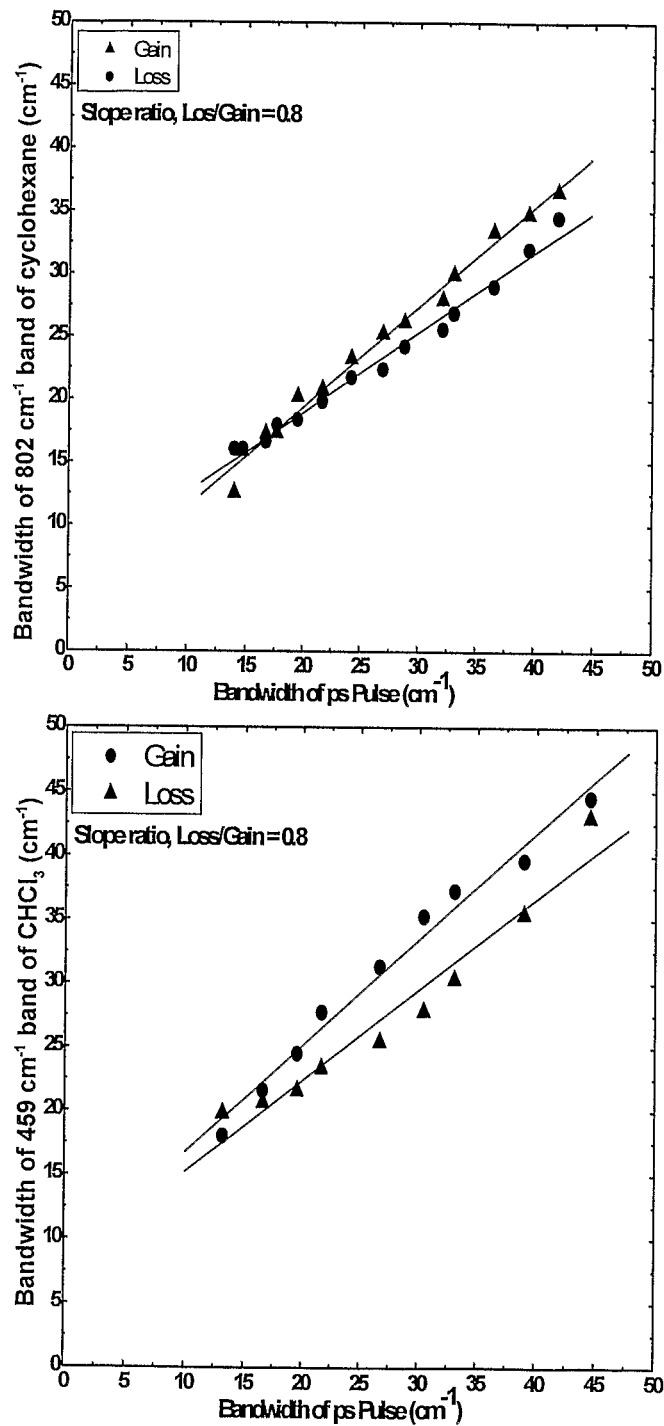

FIG. 14: URLS and SRS signal bandwidth vs the bandwidth of the ps pulse.

Figure 15:
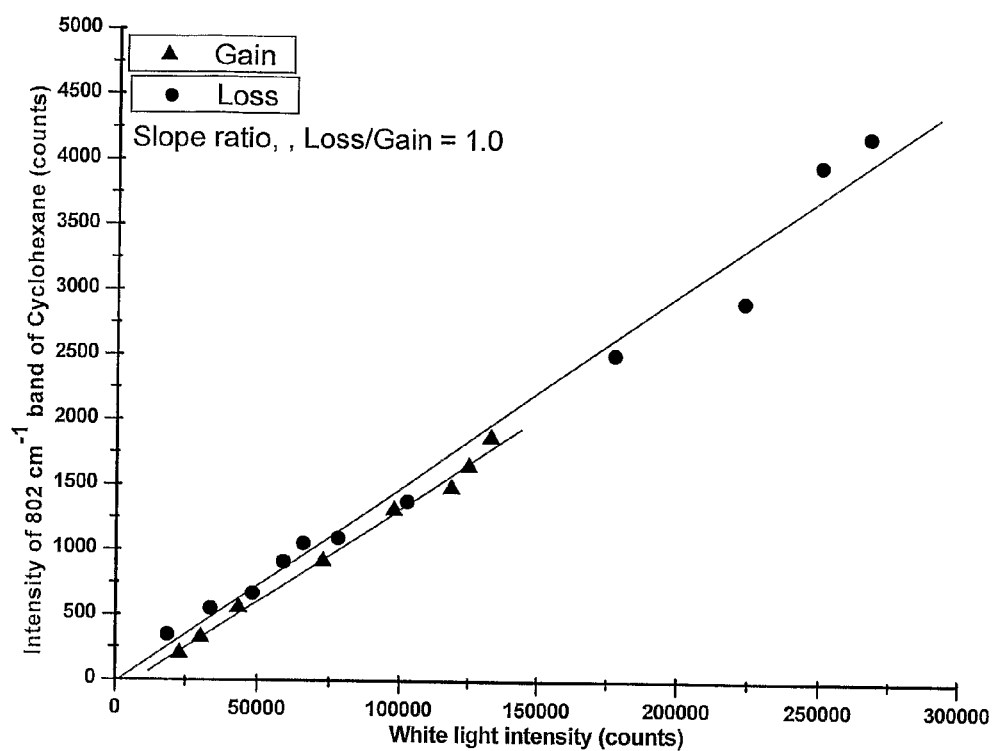

FIG. 15: URLS and SRS signal intensity vs WL power with filters to allow only region of interest with respect to technique used (URLS or SRS).

DETAILED DESCRIPTION OF THE INVENTION

The present invention relates to a method for detecting vibrational structure of a molecule, said method comprising steps of:
 a) generating White Light Continuum (WL) probe and picosecond pump; and
 b) focusing the WL probe and picosecond pump onto a sample temporally and spatially to detect the vibrational structure of the molecule.

In another embodiment of the present invention, the WL is generated by passing a femtosecond pulse generated from a femtosecond source through crystal or a fiber unit.

In yet another embodiment of the present invention, the pulse has a pulse width ranging from about 30 femtosecond to about 500 femtosecond pulse, preferably about 105 femtosecond, and wavelength ranging from about 750 nm to about 840 nm, preferably about 788 nm.

In still another embodiment of the present invention, the crystal unit comprises of an iris, a neutral density filter, and optical lenses surrounding a crystal In still another embodiment of the present inventions, the crystal is a Sapphire or Calcium fluoride crystal.

In still another embodiment of the present invention, the optical lenses are placed at a distance of focal length ranging from about 25.4 mm to about 500 mm.

In still another embodiment of the present inventions, the wavelength of the WL continuum ranges from about 450 nm to about 1000 nm.

In still another embodiment of the present invention, the WL continuum is further allowed to pass through a short wave pass filter to obtain WL continuum probe covering both the Stokes- and anti-Stokes Raman vibrational frequencies, preferably wavelength ranging from about 400 nm to about 750 nm.

In still another embodiment of the present invention, the picosecond pump is generated from a femtosecond pulsed source.

In still another embodiment of the present invention, the femtosecond pulsed source is a tunable femtosecond source providing an output ranging from about 235 nm to about 10 μm, preferably in the region ranging from about 235 nm to about 800 nm.

In still another embodiment of the present invention, the femtosecond pulsed source generated is allowed to pass through a spectral filter to obtain a picosecond pulse in the region ranging from about 235 nm to about 800 nm, preferably about 550 nm with the bandwidth of the output picosecond pulse ranging from about 0.1 cm$^{-1}$ to about 50 cm$^{-1}$.

In still another embodiment of the present invention, the spectral filter consists of two gratings, an adjustable slit and two lenses of focal length ranging from about 25.4 mm to about 500 mm focal length, preferably about 150 mm focal length.

In still another embodiment of the present invention, the spectral filter reduces the bandwidth of the femtosecond pulse to obtain a picosecond pulse in the region ranging from about 235 nm to about 800 nm, preferably about 550 nm with the bandwidth of the output picosecond pulse ranging from about 0.1 cm$^{-1}$ to about 50 cm$^{-1}$.

In still another embodiment of the present invention, the vibrational structure is detected by observing the LOSS signals generated on the higher energy side of the white light continuum with respect to the picosecond pulse wavelength.

The present invention relates to a system for detection of vibrational structure of a molecule, said system comprising of:
 a) a femtosecond source having a light source input, wherein the femtosecond source is configured to generate a femtosecond pulse,
 b) a spectral filter receives the femtosecond pulse generated by the femtosecond source to produce a picosecond pulse, and a crystal unit along with a short wave pass filter receives the femtosecond pulse generated by the femtosecond source to produce white light continuum,
 c) a sample unit receives the picosecond pulse and the white light continuum to provide a signal output, and
 d) a spectrometer takes the signal output generated from the sample unit to produce a signal in spectral domain and a detector to detect vibrational structure of molecule by creating image of the spectral domain signal.

In another embodiment of the present invention, the light source is a laser pump used to generate a femtosecond source.

In yet another embodiment of the present invention, the femtosecond source is generated using plurality of laser oscillators and amplifiers.

In still another embodiment of the present invention, the spectral filter consists of two gratings, an adjustable slit and two lenses of focal length ranging from about 25.4 mm to about 500 mm focal length, preferably about 150 mm focal length.

In still another embodiment of the present invention, the femtosecond pulsed source for picosecond generation is a tunable femtosecond source providing an output ranging from about 235 nm to about 10 μm, preferably in the region ranging from about 235 nm to about 800 nm In still another embodiment of the present invention, the crystal unit comprises of an iris, a neutral density filter, and optical lenses surrounding a crystal In still another embodiment of the present invention, the crystal is a Sapphire or Calcium fluoride crystal.

In still another embodiment of the present invention, the optical lenses are placed at a distance of focal length ranging from about 25.4 mm to about 500 mm.

In still another embodiment of the present invention, the spectral filter produces the picosecond pulse in the region ranging from about 235 nm to about 800 nm, preferably about 550 nm with the bandwidth of the output picosecond pulse ranging from about 0.1 cm$^{-1}$ to about 50 cm$^{-1}$ In still another embodiment of the present invention, the crystal unit produces the WL continuum ranging from about 450 nm to about 1000 nm.

In still another embodiment of the present invention, the short wave pass filter further provides a White Light continuum probe covering both the Stokes- and anti-Stokes Raman vibrational frequencies, preferably wavelength of region ranging from about 400 nm to about 750 nm.

In still another embodiment of the present invention, the detector is a charge coupled device cooled by liquid nitrogen.

The present invention relates to another form of a non-linear technique, which we refer to as Ultra-fast Raman Loss scattering (URLS)[13-15], which provides better signal to noise ratio with a natural 100% fluorescence rejection. This technique is experimentally analogous to stimulated Raman scattering or the SRS[11]. In URLS, signal detection is on the blue side (higher energy) with respect to the excitation wavelength. This is unlike SRS where signal detection is on the red side (lower energy) (FIG. 1) Importantly, URLS signal appears as a loss signal as oppose to gain signal observed in SRS. Some other groups[16-18] also have observed such signals, but in equal magnitude, as gain (SRS) signals. Thus, these groups[16-18] have termed these loss signals as anti-Stokes Raman scattering, similar to the convention used in Raman spectroscopy. However, we have found that the URLS signals are at least 1.5 times more intense than SRS signals. Additionally, the term anti-Stokes implies the emission of signal from a higher energy state to a lower energy state, which is not the case observed in URLS. Thus, the word "anti-Stokes" is quite misleading. Hence, in order to differentiate the process and extra intensity observed, the process is referred to as Ultra-fast Raman Loss Spectroscopy (URLS)[13-15].

The rapid data acquisition, natural fluorescence rejection and experimental ease institute Ultra-fast Raman loss scattering (URLS) as a unique valuable structure determining technique. URLS is an analogue of stimulated Raman scattering (SRS) but more sensitive than SRS. It involves the interaction of the two laser sources, viz. a picosecond (ps) pulse and white light (WL), with a sample leading to the generation of loss signal on the higher energy (blue) side with respect to the wavelength of the ps pulse, unlike the gain signal observed on red side in SRS. These loss signals are at least 1.5 times more intense than SRS signals. Also, the very prerequisite of the experimental protocol for signal detection to be on the higher energy side by design eliminates the interference from fluorescence, which appears on the red side. Unlike CARS, URLS signals are not precluded by non-resonant background under resonance condition and also being a self-phase matched process is experimentally easier. These loss features appear at wavenumbers corresponding to the difference between the ps wavenumber and the characteristic Raman vibrational wavenumbers of the sample. The subtraction of the continuum with the ps pulse ON and OFF gives the loss spectrum.

It is important to note that loss signals on the blue side have been observed previously. Recently, Mathies et. al. have seen such loss (negative) signals but having equal magnitude as the gain signals and attributed them as arising due to a third order ($\chi^{(3)}$) process. These groups have referred to it as "anti-Stokes" loss signal diametric to "Stokes" gain signal in stimulated Raman scattering (SRS). But the word "anti-Stokes" in conventional Raman spectroscopy implies the loss of energy from a higher energy state to a lower energy state, which is not the case in their as well as our studies and hence, it is quite misleading. Notably, in their study the white light (WL) exclusive to the blue or red of the ps pulse was used for loss and gain experiments respectively.

This is unlike the present invention wherein WL spectrum used covers the entire spectral range from blue (−3305 cm$^{-1}$) to red (1652 cm$^{-1}$) with respect to the wavelength of the ps pulse. In other words, the WL used for URLS study was not truncated to cover only the blue region but allows both blue and red regions and vice versa for SRS gain studies. Our experimental conditions led to more intense Raman loss signals compared to the gain SRS signals. From this one can hypothesize that the extra field on the red side plays an important role and is responsible for the extra intensity observed by us on for loss signal.

The present invention is further elaborated with the help of following examples. However, these examples should not be construed to limit the scope of the invention.

EXAMPLE 1

Role of Additional Red Field in Observing Loss Signals with High Intensity

To verify if the additional red field (Stokes region) is responsible for the extra intensity observed by us in URLS, WL power dependence study of both loss and gain signals for two cases have been carried out:

Case 1:

WL covers the entire spectral range from blue to red. A short wave pass filter (FES0600, Thorlabs) is placed on WL path after its generation. This removes the fundamental amplifier beam at 788 nm while transmitting the region from 450 nm to 600 nm. This region corresponds to −3305 cm$^{-1}$ (blue) to 1652 cm$^{-1}$ (red) of the WL with respect to the ps pulse wavelength of 550 nm.

Case 2:

WL truncated only to the region of observation i.e. only red region for Gain experiments and vice versa for loss. The red region was blocked using a short wave pass filter (FES0550, Thorlabs) for URLS study. This will allow only the blue region with respect to the ps wavelength of 550 nm (FIG. 2a). While a long wave pass filter (LPF600, Newport) was used to block the blue region during gain spectrum recording. A long wave pass filter will transmit only the longer wavelengths (with 50% transmission at 600 nm) (FIG. 2b).

Results Observed

For Case 1:

FIG. 3 shows URLS and SRS signal intensity change for 992 cm$^{-1}$ band of benzene with the variation in power of WL. Both loss and gain signal intensities were found to depend linearly on WL power. However, URLS signal is at least 1.8 times more intense and sensitive than SRS gain signal to WL power.

For Case 2:

FIG. 4 illustrates the change observed in the URLS and SRS signal intensities for 802 cm$^{-1}$ band of cyclohexane with variation in WL power. It is evident from FIG. 4 that both the intensities not only vary linearly, but with the same slope unlike in earlier study when the WL was not truncated (FIG. 3). This confirms our idea that the additional intensity observed might be arising due further interaction of a third order process with another photon leading to some higher order process.

EXAMPLE 2

Experimental Set-up of the System used to Perform URLS

URLS is a non-linear technique analogous to stimulated Raman gain spectroscopy (SRS), involving a femtosecond (fs) broadband continuum and a picosecond (ps) narrow bandwidth pulses.

URLS setup involves two pulses, viz. a narrow bandwidth (7-25 $cm^{-1}$) ps pulse and a white light (WL) continuum covering the molecular vibrational frequencies. Both the pulses are generated from a 100 fs laser system as discussed below.

Laser System:

Laser system (FIG. 5) includes a Ti: Sapphire Regenerative Amplifier (Spitfire, Spectra Physics) seeded by a Mode-Locked Ti: Sapphire laser (110 fs, 8.75 nJ, 80 MHz, Tsunami, Spectra Physics). The amplifier generates a 105 fs pulse at a repetition rate of 1 KHz and having a pulse energy of 2.2 mJ centered at 788 nm. About ~1 mJ of the amplifier output is used to pump an Optical Parametric Amplifier (OPA).

ps Pulse:

The OPA generates 86 fs pulse centered at 550 nm, which is used to produce the ps pulse using a spectral filter. The spectral filter consists of two gratings (1200 g/mm, 750 nm blaze), two lenses (150 mm focal length) and an adjustable slit. The design of the spectral filter is shown in FIG. 6. The OPA output is attenuated by an aperture to a beam of size 4 mm and energy 3.7 µJ and incident on the first grating. The grating disperses the beam spectrally. The lens placed at the focal distance from the grating laterally focuses each of the spectral components of the dispersed beam on to the slit. According to the frequency-time uncertainty principle, a smaller BW implies a longer pulse in time domain and vice-versa. Thus, the pulse width of the output beam is determined by the width of the slit while the lateral position determines the central wavelength of the output beam. Typically, the slit width is kept so as to obtain a ps pulse as an output. Then the second lens collimates the beam followed by the second grating that removes the angular dispersion. Importantly, all the components of the spectral filter are positioned at focal distance. This ensures the reduction in group velocity (GVD) experienced by the beam and also to remove angular dispersion. A ps pulse centered at 550.3 nm with BW and pulse energy of 25 $cm^{-1}$ and 209 nJ respectively obtained using the spectral filter is shown in FIG. 6

Spectral Filter:

The ps pump is generated by spectrally filtering the OPA output using a home designed spectral filter. The spectral filter consists of two gratings (1200 g/mm, 750 nm blaze), an adjustable slit and two lenses of 150 mm focal length. The distance between each component is equal to the focal length of the lens. This arrangement reduces the angular dispersion as well as the group velocity dispersion (GVD) experienced by the beam. The OPA output is attenuated by an aperture to a beam of size 4 mm and energy 3.7 µJ, and incident on the first grating (Grating1), which disperses the beam in spectral domain.

The first lens focuses each of the spectral components of the dispersed beam laterally on to the slit. Now, according to the frequency-time uncertainty principle, a narrow spectral width (BW) implies a longer duration pulse. Thus, the width of the slit, i.e. the spectral range allowed, decides the pulse width (Δt) of the pulse obtained. Typically, the slit width is adjusted to obtain a ps pulse, i.e. a narrow BW. The wavelength of the ps pulse is determined by the lateral position of the slit. Then, the second lens collimates the beam while the second grating (Grating 2) removes the angular dispersion.

FIG. 6a displays the ps pulse obtained using ~2.5 µJ of OPA output centered at 550.33 nm. The ps pulse produced is centered at 550.30 nm with BW and energy of 25.38 $cm^{-1}$ and 207 nJ respectively.

WL Continuum:

Rest of the amplifier output is used to produce the WL using a nonlinear crystal, Sapphire (Sa). After attenuating the amplifier output to a beam of size 3 mm and energy 1.5 µJ, it is focused onto a 2 mm Sa crystal for generating WL. A stable and smooth WL is obtained by adjusting the focal point in the crystal and the input amplifier beam energy with the help of the combination of a neutral density filer and an iris. In order to obtain a good WL, initially the beam is focused outside the Sa and then the crystal is slowly translated towards the focal point while simultaneously adjusting the energy of the beam. This is continued till a smooth and stable WL is obtained. The WL obtained ranges from 450 nm to 1000 nm. A short wave pass filter (FES0600) is used to transmit only the region from 450 nm to 600 nm while importantly removing the fundamental amplifier output at 788 nm (FIG. 7). This region covers the Raman shifts ranging from −3305 $cm^{-1}$ to 1652 $cm^{-1}$.

Data Collection:

A non-collinear geometry is used for focusing the two beams, viz. ps and WL, at the sample point. This ensures that no ps pulse is imaged on to the detector. At first, the WL is aligned with respect to the optic axis of the spectrometer (TRIAX 550). Then the WL is focused to a size of 30 µm at the sample point using a lens of focal length 200 mm. Another spherical lens (100 mm) is used to focus the ps pulse at the sample point. Both the beams are spatially and temporally overlapped at the sample point. For most of the studies presented here, a sample cell of either 1 mm or 10 mm path length was used. The WL containing the URLS signal is collected using a lens of focal length 75.6 mm and focused on to the slit of the spectrometer (TRIAX 550) connected to a $LN_2$ cooled CCD. The URLS spectrum is retrieved by subtracting the WL containing the signal from the WL without the signal, i.e.

URLS spectrum=[WL with ps pulse ON]−[WL with ps pulse OFF]

The URLS spectra obtained is baseline corrected using ORIGIN. We recorded the URLS spectra for various systems to demonstrate the performance and understand the principle of URLS.

FIG. 1 shows nonlinear effect observed on white light (WL) on interaction of WL and a ps pulse with a sample. One observes loss (negative) signals on the higher energy side while gain (positive) signals on the lower energy side. Under present experimental condition and setup the loss signals observed are of higher intensity than the gain signals.

EXAMPLE 3

Method for Performing the Experiment

The present invention can be defined by the way of stepwise process as reflected by below:

[1] Generation of the White Light continuum (WL):
  1) Attenuate amplifier output to a beam of size 3 mm and energy 1.5 µJ.
  2) Focus the amplifier beam outside a 2 mm Sapphire crystal.

3) Translate the crystal slowly towards the focal point while simultaneously adjusting the energy of the beam using the neutral density (ND) filter.
4) Continue 2 and 4 till a smooth and stable WL is obtained.
5) Place a short wave pass filter to block the 788 nm amplifier beam and transmit the region 400 nm to 600 nm. This region covers the Raman shifts ranging from $-3305$ cm$^{-1}$ to 1652 cm$^{-1}$.

[2] Generation of the picosecond pulse:
1) Attenuate OPA output to a beam of size 4 mm and energy 3.7 µJ.
2) Incident on grating1 which spectrally disperses the beam.
3) Focus the dispersed beam using a lens placed at a focal distance (150 mm).
4) Using an adjustable slit placed at the focal distance from the lens reduce the bandwidth of the dispersed beam to 0.8 nm. This bandwidth corresponds to a bandwidth of 25 cm$^{-1}$ for a pulse centered at 550 nm.
5) Adjust the lateral position of the slit so as to obtain the desired central wavelength of the ps pulse.
6) Collimate the beam using another lens again placed at the focal point (150 mm).
7) Using grating2 placed at the focal distance remove the angular dispersion.

[3] Align the WL beam along the spectrometer connected to a LN$_2$ cooled CCD detector.

[4] Focus the WL using a 200 mm focal length lens at the sample point.

[5] The ps pulse is focused at the sample point using another lens of focal length 100 mm.

[6] The WL containing the signal is collected using a lens and focused on to the spectrometer slit.

[7] Loss signal is observed as negative signal on top of the blue side of WL with respect to the ps pulse wavelength.

[8] WL spectrum is recorded with and without the ps pulse (blocking ps pulse with blocker).

[9] The difference between the WL spectrum with and without ps pulse gives the LOSS SPECTRUM.

[10] Ensure that both the beams are spatially well overlapped using a pin hole of diameter 100 micron.

[11] The temporal overlap is adjusted by making the ps pulse pass through a motor controlled delay generator.

[12] The time delay between the pulses is adjusted till the maximum signal of the sample (benzene) is obtained.

An important criterion is the position of the optics for generation of the WL and ps pulse.

Another important fact is the use of correct filter on the path of WL to make sure both red and blue region are present with respect to the ps pulse wavelength.

Since it is a femtosecond pulse, one should use mirrors to reflect the beam (by 90 degree) to follow the beam path instead of prism which causes Group Velocity Dispersion and broadens the pulse in time domain.

One should use least possible dispersive elements such as lenses so as to reduce Group Velocity Dispersion.

It can be observed in FIG. 8 that Change in URLS signal of the $-992$ cm$^{-1}$ peak of benzene with the change in delay between the ps pulse and WL. URLS signal intensity was found to decrease as the delay between the two pulses was changed in either direction, viz. negative or positive from the zero delay. That is, the signal intensity decreases as the overlap between the two pulses reduces.

EXAMPLE 4

Experimental Observations for Different Samples

As an example to detect vibrational spectrum of a molecular species, the Raman Loss Spectra of many chemical solvents were observed.

URLS spectra of (a) Chloroform (CHCl$_3$), (b) Dimethyl Sulphoxide (DMSO), (c) Acetonitrile (ACN), (d) Cyclohexane (CH) and (e) Crystal violet (CV) solution in ethanol are observed (FIG. 9a). The peaks correspond to the characteristic vibrational frequencies of each molecule in delta wavenumbers or Raman shift. The Raman shift value implies the wavenumber value with respect to the ps wavelength (which corresponds to 0 wavenumber) . . . i.e.

$$\Delta\bar{\theta} = \left(\frac{1}{\lambda\text{ps}} - \frac{1}{\lambda\text{signal}}\right);$$

$\lambda\text{ps}$ = ps pulse wavelength, $\lambda\text{signal}$ = vibrational frequency in wavelength and $\Delta\bar{\theta}$ = Raman shift.

For example, $-670$ cm$^{-1}$ implies $\lambda\text{signal}$=530.45 nm for $\lambda\text{ps}$=550 nm.
$\lambda\text{ps}$=550 nm=>$\bar{\theta}$ps=18181.81 cm$^{-1}$;
$\lambda\text{signal}$=530.45 nm=>$\bar{\theta}$signal=18351.92 cm$^{-1}$.
Thus, $\Delta\bar{\theta}$ps=670.11 cm$^{-1}$.

URLS Spectra of Benzonitrile and Ethanol are Also Shown in FIG. 9b

The spectral pattern observed in URLS is similar to that in normal Raman spectroscopy[19,20]. This indicates that URLS signal intensity must be linearly proportional to non-linear susceptibility unlike CARS. In CARS, it is linearly proportional to the square of third-order susceptibility and thus, leading to more enhancement of modes with strong Raman cross-section at the expense of the weaker ones.

The example also provides to demonstrate recording vibrational spectrum of fluorescent sample. FIG. 9c shows the Raman loss spectrum in detail recorded for crystal violet, which is a well known highly fluorescent dye. Crystal violet is a well-known fluorescent system with an absorption maximum at 588 nm. The URLS spectrum for the CV solution in ethanol was obtained using a ps pulse wavelength centered at 593 nm. The bandwidth of the ps pulse used was 17.5 cm$^{-1}$ and its pulse energy was 260 nJ. Thus FIG. 9c clearly shows that URLS spectrum can be easily recorded for any fluorescent system. This is an inherent characteristic of URLS by virtue of the very design of its experimental protocol. That is, since the URLS spectrum is obtained by recording on the higher energy (blue) side with respect to the wavelength of the ps pulse, the fluorescence that appears on the lower energy (red) side does not interfere with it. Hence, the vibrational structural information of any fluorescent system can be obtained from URLS without any difficulty. Additionally, URLS signals are undistorted under resonance case which is a major problem in CARS. In CARS, the signals are usually distorted due to non-resonant background making data interpretation difficult[1 2].

EXAMPLE 5

Comparative Details of URLS with Respect to SRS and CARS

SRS and CARS are both a third order non-linear ($\chi^{(3)}(\omega_4; \omega_1,\omega_2,\omega_3)$) process involving the interaction of a medium with three optical photons ($\omega_1, \omega_2, \omega_3$) to generate a fourth photon ($\omega_4$). The first two photons ($\omega_1$ and $\omega_2$) interact with the system to create a vibrational coherence ($\omega_v$). This vibrational coherence then interacts with the third photon ($\omega_3$) to produce a directional signal beam ($\omega_4$) ($k_1+k_2-k_3=k_4$). However, the physical process involving the creation of coherence created and the interaction of the coherence with the third photon are different for CARS and SRS.

The energy level diagram as shown in FIG. 10 explains the physical processes involved in SRS and CARS. The comparative details of URLS with respect to SRS and CARS are given in table 1 below:

TABLE 1

Comparitive details of URLS with respect to SRS and CARS

| URLS | SRS | CARS |
| --- | --- | --- |
| Coherent process | Coherent process | Coherent process |
| Self phase matched | Self phase matched | Specific phase matching required; incoming laser tuning required |
| Experimentally easier | Experimentally easier | |
| higher-order nonlinear | third-order nonlinear [$\chi^{(3)}$] | third-order nonlinear [$\chi^{(3)}$] |
| Un-distorted signal; no non-resonant background | Un-distorted signal; no non-resonant background | sensitivity is limited due to signal distortion due to non-resonant background; data interpretation difficult |
| No signal distortion under resonance condition | — | Signals are dispersive under resonance (res) conditions due to the non-resonant background arising from solvent molecules. |
| Found pattern to be same as in normal Raman scattering indicating linearly proportional to [$\chi^{(n)}$] | Signal is linearly proportional to [$\chi^{(3)}$], equal enhancement | Signal is directly proportional to square of [$\chi^{(3)}$] i.e. vibrational modes with strong Raman cross-section are enhanced more at the expense of weaker ones. |
| Much simpler | Much simpler | Methods to reduce non-resonant background have been developed; but require additional optical and electronic components and thus, experimentally complex. |
| 1.5 to 2.0 times more intense than SRS gain | 1.5 to 2.0 times weaker than URLS signal | — |
| Natural complete fluorescence rejection | Efficient but not complete fluorescence rejection | Efficient fluorescence rejection |

URLS is an analogue of stimulated Raman scattering (SRS) but more sensitive than SRS with better signal to noise ratio. It involves the interaction of the two laser sources, viz. a picosecond (ps) pulse and white light (WL), with a sample leading to the generation of loss signal on the higher energy (blue) side with respect to the wavelength of the ps pulse unlike the gain signal observed on red side in SRS. These loss signals are at least 1.5 times more intense than SRS signals. Furthermore, the very requirement of the experimental protocol for signal detection to be on the higher energy side by design eliminates the interference from fluorescence, which appears on the red side. That is, URLS leads to natural fluorescence rejection. Unlike CARS, URLS signals are not precluded by non-resonant background under resonance condition and also being a self-phase matched process is experimentally easier.

FIG. 11 shows the comparison of URLS and SRS spectra of (a) CHCl$_3$, (b) ACN and (c) CCl4. It is quite evident from the figure that Loss signal is more intense than Gain signal by a factor 1.5-2.0. The peaks correspond to the characteristic vibrational frequencies of each molecule in delta wavenumbers or Raman shift. Thus, a URLS spectrum can be recorded at an acquisition time at least 1.5 lesser than that required for SRS.

Power Dependence of WL and ps:

The change in URLS and SRS signal intensity was observed as a function of the WL energy using CHCl$_3$ and CH. FIG. 12 shows URLS and SRS signal intensity vs WL power. The graph shows that both the process (gain and loss) are linearly dependent on the WL power. However, from FIG. 12 it is apparent that at low powers of WL, both the scattering have same magnitude. From FIG. 12 it is apparent that at low powers of WL, both the scattering have same magnitude. However, their slopes are different. Loss is about 1.5-2.5 times more intense than gain.

Interestingly, the same pattern was observed as the ps pulse energy is varied (FIG. 13). The extra intensity observed for URLS signal compared to SRS ($\chi^{[3]}$ process) might be due to some additional process other than just $\chi^{[3]}$ process.

The example further shows URLS and SRS signal intensity vs WL power with filters to allow only region of interest with respect to technique used (URLS or SRS), as observed in FIG. 15 It illustrates the change observed in the URLS and SRS signal intensities for 802 cm$^{-1}$ band of cyclohexane with variation in WL power. It is evident that both the intensities not only vary linearly but with the same slope unlike in earlier study when the WL was not truncated. This confirms that the additional intensity observed might be arising due further interaction of a third order process with another photon leading to some higher order process.

Bandwidth Dependence of URLS Signal of ps Pulse Bandwidth:

URLS signal bandwidth vs the bandwidth of the ps pulse is also compared in the present example. FIG. 14 shows the bandwidth change is linear with respect to the ps bandwidth indication that the spectral resolution is greatly determined by the ps pulse width.

All the examples cited above demonstrate explicitly that URLS is a better technique than SRS by being more sensitive and providing a complete natural fluorescence rejection. From the power dependence study, it is quite apparent that the loss signal observed in the present invention is not just mere "anti-Stokes" SRS signal as reported by others wherein the loss signal observed was as intense as the gain (Stokes) signal. The loss signal observed in the present invention unmistakably is more intense than the gain (SRS) signal. Thus, these loss signal observed are not just due to the third order non-linear process like SRS but some higher order process contributing to the extra intensity.

In summary, Ultra-fast Raman Loss scattering (URLS) has been presented as a novel structure elucidating tool. It has been demonstrated that it can also provide the vibrational information of fluorescent system with a complete and natural rejection of fluorescence. It is established that it is much more sensitive and effective than SRS with rapid data acquisition time. Unlike CARS, URLS signals are not contorted under resonance condition due to any non-resonant background. Furthermore, URLS is a coherent and self-phase matched process, thus experimentally easier than CARS.

We claim:

1. A method for detecting vibrational structure of a molecule, said method comprising:
    generating White Light Continuum (WL) probe and picosecond pump, said picosecond pump is generated from a femtosecond pulsed source which is passed through a spectral filter to obtain a picosecond pulse of a predetermined range, the WL probe being generated by filtering the WL continuum using a short wave pass filter, and the WL probe covering both the Stokes and anti-Stokes Raman vibrational frequencies;

focusing the WL probe and the picosecond pump onto a sample temporally and spatially;

collecting a WL signal generated with the picosecond pump and WL signal generated without the picosecond pump after focusing the WL probe and the picosecond pump onto a sample; and obtaining a WL spectrum from the collected WL signal generated with and without the picosecond pump, said WL spectrum covering the spectral region ranging from Stokes to anti-Stokes Raman vibrational frequencies to detect the vibrational structure of the molecule;

wherein intensity of loss signal on anti-Stokes side is more than the intensity of gain signal on Stokes side of the spectral region.

2. The method as claimed in claim 1, wherein said WL probe is generated by passing a femtosecond pulse generated from a femtosecond source through a fiber unit.

3. The method as claimed in claim 2, wherein the femtosecond pulse has a pulse width ranging from 30 femtoseconds to 500 femtoseconds, and wavelength ranging from 750 nm to 840 nm.

4. The method as claimed in claim 1, wherein said WL probe is generated by passing a femtosecond pulse generated from a femtosecond source through a crystal unit, wherein the crystal unit comprises of an iris, a neutral density filter, and optical lenses surrounding a crystal.

5. The method as claimed in claim 4, wherein the crystal is a Sapphire or Calcium fluoride crystal; and the optical lenses are placed at a distance of focal length ranging from about 25.4 mm to about 500 mm.

6. The method as claimed in claim 2, wherein the wavelength of the WL ranges from 450 nm to 1000 nm.

7. The method as claimed in claim 6, wherein the WL probe obtained from the short wave pass filter covering both the Stokes and anti-Stokes Raman vibrational frequencies, comprises a wavelength ranging from about 400 nm to about 750 nm.

8. The method as claimed in claim 1, wherein the femtosecond pulsed source is a tunable femtosecond source, providing an output ranging from 235 nm to 800 nm.

9. The method as claimed in claim 1, wherein-the predetermined range of picosecond pulse is from 235 nm to 800 nm, with the bandwidth of the output picosecond pulse ranging from about 0.1 $cm^{-1}$ to about 50 $cm^{-1}$.

10. The method as claimed in claim 1, wherein the spectral filter consists of two gratings, an adjustable slit and two lenses of focal length ranging from 25.4 mm to 500 mm focal length.

11. The method as claimed in claim 1, wherein the spectral filter reduces the bandwidth of the femtosecond pulse to obtain a picosecond pulse in the region ranging from 235 nm to 800 nm, with the bandwidth of the output picosecond pulse ranging from about 0.1 $cm^{-1}$ to about 50 $cm^{-1}$.

12. The method as claimed in claim 1, wherein the vibrational structure is detected by observing the LOSS signals generated on the higher energy side of the WL with respect to the picosecond pulse wavelength.

13. A system for detection of vibrational structure of a molecule, said system comprising:
   a femtosecond source having a light source input, wherein the femtosecond source is configured to generate a femtosecond pulse,
   a spectral filter to receive the generated femtosecond pulse, said spectral filter comprises two gratings, an adjustable slit and two lenses to produce the picosecond pulse of predefined bandwidth range;
   an amplifier to generate a femtosecond pulse, said femtosecond pulse is transmitted through a crystal unit to produce White Light (WL) Continuum;
   a short wave pass filter to allow Stokes and anti-Stokes Raman vibrational frequencies corresponding to the wavelength of picosecond pulse within the WL Continuum;
   a sample unit to receives the picosecond pulse and the white light continuum, focusing the received picosecond pulse and white light continuum at a predefined sample to generate a signal output;
   a spectrometer to receive the signal output generated from the sample unit to produce a signal in spectral domain, said produced signal is a WL spectrum which covers the spectral region ranging from Stokes to anti-Stokes Raman vibrational frequencies; and a detector to detect vibrational structure of molecule from the spectral region ranging from Stokes to anti-Stokes Raman vibrational frequencies, wherein intensity of loss signal on the Stokes side is less than intensity of gain signal on the anti-Stokes side of the spectral region.

14. The system as claimed in claim 13, wherein the femtosecond source is generated using a laser pump or using a plurality of laser oscillators and amplifiers.

15. The system as claimed in claim 13, wherein the spectral filter consists of two gratings, an adjustable slit and two lenses of focal length ranging from 25.4 mm to 500 mm focal length.

16. The system as claimed in claim 13, wherein the femtosecond pulsed source for picosecond generation is a tunable femtosecond source providing an output ranging from 235 nm to 800 nm.

17. The system as claimed in claim 13, wherein the crystal unit comprises of an iris, a neutral density filter, and optical lenses surrounding a crystal.

18. The method as claimed in claim 17, wherein the crystal is a Sapphire or Calcium fluoride crystal; and the optical lenses are placed at a distance of focal length ranging from 25.4 mm to 500 mm.

19. The system as claimed in claim 13, wherein the spectral filter produces the picosecond pulse in the region ranging from 235 nm to 800 nm, with the bandwidth of the output picosecond pulse ranging from about 0.1 $cm^{-1}$ to about 50 $cm^{-1}$.

20. The system as claimed in claim 13, wherein the crystal unit produces the WL ranging from 450 nm to-1000 nm.

21. The system as claimed in claim 13, wherein the short wave pass filter further provides a WL probe covering both the Stokes and anti-Stokes Raman vibrational frequencies, with wavelength ranging from 400 nm to 750 nm.

22. The system as claimed in claim 13, wherein the detector is a charge coupled device cooled by liquid nitrogen.

* * * * *